United States Patent [19]

Cox

[11] 4,224,936

[45] Sep. 30, 1980

[54] TRANSIT ISOLATOR

[75] Inventor: Walter H. Cox, Weybridge, England

[73] Assignee: Vickers Limited, London, England

[21] Appl. No.: 44,228

[22] Filed: May 31, 1979

[30] Foreign Application Priority Data

May 31, 1978 [GB] United Kingdom ............... 25417/78

[51] Int. Cl.[3] .............................................. A61F 13/00

[52] U.S. Cl. .................................... 128/132 R; 5/81 B

[58] Field of Search .................... 128/132 R, 1 B, 184, 128/191 A, 298; 5/81 R, 81 B, 81 C, 82 R, 85; 4/177

[56] References Cited

U.S. PATENT DOCUMENTS

| | | | |
|---|---|---|---|
| 2,272,778 | 2/1942 | Reuter | 5/81 B |
| 2,733,452 | 2/1956 | Tanney | 5/81 B |
| 3,076,451 | 2/1963 | Stoner | 128/1 B |
| 3,293,668 | 12/1966 | Auer | 5/81 R |
| 3,452,371 | 7/1969 | Hirsch | 5/81 B |
| 3,469,266 | 9/1969 | Hyde | 4/177 |
| 3,490,443 | 1/1970 | Decupper | 128/1 B |
| 3,905,055 | 9/1975 | Blair | 5/85 |
| 3,938,203 | 2/1976 | Linard | 5/81 R |

*Primary Examiner*—Lawrence W. Trapp

*Attorney, Agent, or Firm*—Larson, Taylor and Hinds

[57] ABSTRACT

A transit isolator which comprises: (i) a first frame including (a) a pair of spaced generally parallel horizontal members, from which is slidably suspended an isolator in the form of a flexible film envelope having a plurality of sleeves in the sides thereof, (b) a basal structure, preferably comprising a stretcher, adapted to support said horizontal members, and (c) an end frame defining a closable port through which a patient may be conveyed into and out of the flexible film envelope; and (ii) a second frame comprising an end section adapted to slide along the horizontal members of said first frame and to which is attached that end of said flexible film envelope remote from the closable port, whereby movement of said end section along the horizontal members of the first frame causes the flexible film envelope to become compressed in the manner of a concertina in the direction towards said closable port.

4 Claims, 2 Drawing Figures

TRANSIT ISOLATOR

BACKGROUND OF THE INVENTION

This invention relates to a transit isolator which may be used to convey a patient under isolated conditions and then to transfer him from the transit isolator into another isolator which may be linked to the transit isolator by a microbiologically secure transfer tunnel.

Isolators, also known as isolation enclosure apparatus, may be used, for example, to protect a hypersensitive patient from micro-organisms in the general environment (in which case the isolator is maintained at a pressure slightly higher than ambient atmospheric pressure) or in the treatment of a patient suffering from a highly infectious disease (in which case the isolator is maintained at a pressure slightly lower than ambient atmospheric pressure).

SUMMARY OF THE INVENTION

According to the present invention, there is provided a transit isolator which comprises: (i) a first frame including (a) a pair of spaced generally parallel horizontal members, from which is slidably suspended an isolator in the form of a flexible film envelope having a plurality of sleeves in the sides thereof, (b) a basal structure adapted to support said horizontal members, and (c) an end frame defining a closable port through which a patient may be conveyed into and out of the flexible film envelope; and (ii) a second frame comprising an end section adapted to slide along the horizontal members of said first frame and to which is attached that end of said flexible film envelope remote from the closable port, whereby movement of said end section along the horizontal members of the first frame causes the flexible film envelope to become compressed in the manner of a concertina in the direction towards said closable port.

DESCRIPTION OF THE PREFERRED EMBODIMENTS

Preferably, the basal structure of the first frame is in the form of a stretcher.

The slidable end section of the second frame is advantageously mounted on the horizontal members of the first frame by means of low friction bearing blocks. Ancillary equipment, for example, an air supply system for the isolator, can be mounted on the second frame so that when the end section of the second frame slides along the horizontal members of the first frame, the ancillary equipment (as well as the end section of the second frame itself) move within the area bounded by the first frame.

The flexible film envelope may be formed from a synthetic polymeric material, e.g. polyvinyl chloride.

BRIEF DESCRIPTION OF THE DRAWINGS

For a better understanding of the invention, and to show how the same may be carried into effect, reference will now be made, by way of example, to the accompanying drawings, in which.

Figure 1:
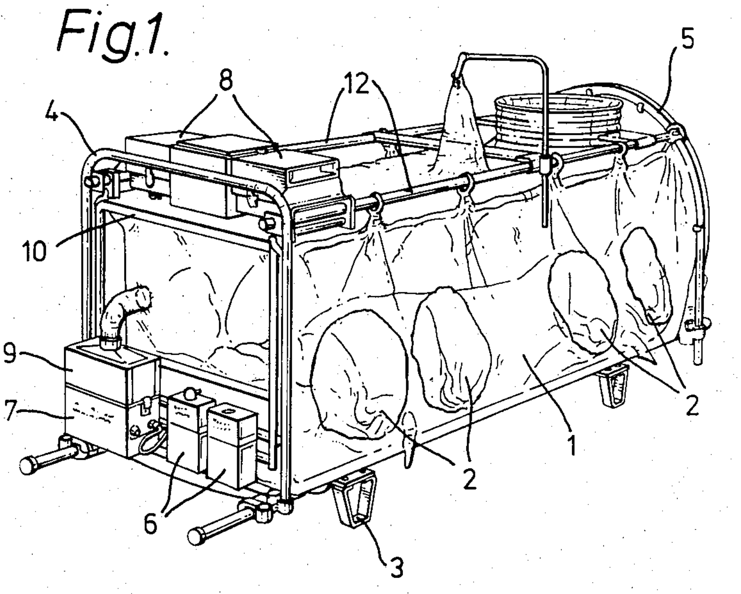
FIG. 1 is an isometric view of one embodiment of the invention.

Referring to the drawings, the transit isolator comprises a flexible film envelope isolator 1 provided with four pairs of gloved sleeves 2, two pairs each on opposite sides of the envelope. A first frame structure comprises a pair of parallel horizontal rods 12 secured to an end member 4 as shown. End member 4 is attached to a basal structure 3 which is in the form of a stretcher. At the end of the first frame opposite to member 4, there is an elliptical frame member 5 which defines a closable port through which a patient may enter or leave the isolator.

Figure 2:
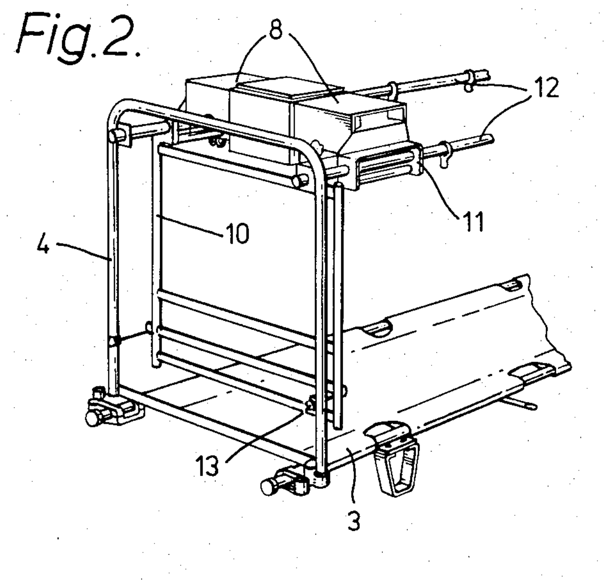
FIG. 2 illustrates part of the embodiment shown in FIG. 1.

A second frame comprises an end section 10 to which one end of the flexible film envelope 1 is attached. The end section 10 can ride along horizontal rods 12 by means of two low friction bearing blocks 11 to which it is attached (see FIG. 2). Mounted on end section 10 and bearing blocks 11 there is an air supply system consisting of batteries 6, a motor blower unit 7, input filters 8 and an output filter 9. The second frame can be secured to end member 4 of the first frame through releasable screws or clips 13.

When in use, a patient is introduced into the transit isolator through a port defined by frame member 5. Within the isolator 1, the patient rests on a canvas wrap (not shown). When the patient within the isolator is to be moved from one location to another, screws or clips 13 are fastened so that members 4 and 10 are secured together. When a patient is to be transferred from the transit isolator into another isolator, the transit isolator is placed with port 5 contiguous with the entry port of the other isolator, or contiguous with a microbiologically secure transfer tunnel leading to the other isolator. Screws or clips 13 are then released, so that operating personnel can lift the patient by means of the canvas wrap (operating via sleeves 2) from the surface of the stretcher 3 and convey him through the port 5. Simultaneously, end section 10 and the ancillary equipment mounted thereon and on blocks 11 are caused to slide along horizontal rods 12, thus causing the flexible film envelope 1 to become compressed and folded on itself in the manner of a concertina. During this operation, the air supply system, and any other ancillary equipment provided, continues to function normally. Thus the patient should not be subjected to risk as a result of the transfer operation. Furthermore, by means of apparatus of this invention it may be possible to use fewer attendants than is conventionally the case when a patient is transferred from one isolating unit to another.

What is claimed is:

1. A transit isolator which comprises: (i) a first frame including (a) a pair of spaced generally parallel horizontal members, from which is slidably suspended an isolator in the form of a flexible film envelope having a plurality of sleeves in the sides thereof, (b) a basal structure adapted to support said horizontal members, and (c) an end frame defining a closable port through which a patient may be conveyed into and out of the flexible film envelope; and (ii) a second frame comprising an end section adapted to slide along the horizontal members of said first frame and to which is attached that end of said flexible film envelope remote from the closable port, whereby movement of said end section along the horizontal members of the first frame causes the flexible film envelope to become compressed in the manner of a concertina in the direction towards said closable port.

2. An isolator as claimed in claim 1, wherein the basal structure of said first frame comprises a stretcher.

3. An isolator as claimed in claim 2, wherein the said end section of the second frame is mounted on the horizontal members of the first frame by means of low friction bearing blocks.

4. An isolator as claimed in claim 2, wherein an air supply system for the isolator is attached to the second frame.

* * * * *